United States Patent [19]

Horn

[11] Patent Number: 4,917,101
[45] Date of Patent: Apr. 17, 1990

[54] VENA PUNCTURE DEVICE AND METHOD

[76] Inventor: Daniel P. Horn, 516 Belmont Pkwy., Sleepy Hollow, Ill. 60118

[21] Appl. No.: 315,600

[22] Filed: Feb. 27, 1989

[51] Int. Cl.⁴ ............................................. A61B 5/00
[52] U.S. Cl. ................................... 128/763; 604/403
[58] Field of Search .................. 128/763, 764, 770; 604/51, 52, 187, 264, 272, 403

[56] References Cited

U.S. PATENT DOCUMENTS

| | | | |
|---|---|---|---|
| 2,639,709 | 5/1953 | Volgenau | 128/764 |
| 2,667,986 | 2/1954 | Perelson | 215/228 |
| 2,880,723 | 4/1959 | Adams | 604/193 |
| 3,159,159 | 12/1964 | Cohen | 128/766 |
| 3,401,693 | 9/1968 | Cohen | 604/192 |
| 3,503,386 | 3/1970 | Pieratt | 128/764 |
| 3,528,404 | 9/1070 | Chan | 128/762 |
| 3,757,779 | 9/1973 | Rovinski | 604/190 |
| 3,931,815 | 1/1976 | Takatsuki | 128/764 |
| 4,617,016 | 10/1986 | Blomberg | 604/155 |
| 4,676,775 | 6/1987 | Zolnierczyk et al. | 604/28 |
| 4,747,414 | 5/1989 | Brossel | 128/754 |
| 4,790,827 | 12/1988 | Haber et al. | 604/198 |
| 4,813,426 | 3/1989 | Haber et al. | 128/763 |
| 4,846,808 | 7/1989 | Haber et al. | 128/763 |

FOREIGN PATENT DOCUMENTS

| | | | |
|---|---|---|---|
| 771890 | 10/1934 | France | 128/763 |
| 2564726 | 11/1985 | France | 128/763 |

*Primary Examiner*—Max Hindenburg
*Attorney, Agent, or Firm*—Mathew R. P. Perrone, Jr.

[57] ABSTRACT

A vena puncture device has a modified vena tube to provide for a spring loaded assembly within the vena tube. With the spring loaded assembly, the compressed spring of the vena puncture device provides for simplifed removal of a vacuum tube. Latches release the compressed spring assembly forcing the vacuum tube out of the vena tube and minimizing the pulling on the needle thereby easing the pain to the patient.

18 Claims, 1 Drawing Sheet

VENA PUNCTURE DEVICE AND METHOD

BACKGROUND OF THE INVENTION

This invention relates to a medical device and more particularly to an improved vena puncture (or medical) device and method for drawing blood.

As is customary in many medical procedures, a substantial number of blood samples of about five (5) to ten (10) cubic centimeters are drawn from the patient to provide a specimen or specimens for a variety of tests. These tests can indicate a method of treatment, a type of illness and provide other useful information about the health of the person. A primary method of drawing blood is to insert a needle in the arm. The blood is then withdrawn through the needle and used in the various testing procedures.

In order to avoid multiple probings required by a number of different samples of blood for different tests, a vena puncture device is known medical instrument. A standard vena puncture device includes a hollow, cylindrical needle having a sharpened point for puncturing and an opening at both ends mounted in a tubular member. One end of needle is outside the tube and serves to puncture the vein. At the other end of the needle, which is inside the tube, a sealed vacuum tube is applied such that the needle within the vena puncture tube punctures the vacuum seal of the vacuum tube. The vacuum then draws blood into the vacuum tube.

This vena puncture device reduces the number of punctures that must be made in the vein to one for the purpose of drawing blood. Only one puncture is made. As many vacuum tubes as required are used for samples. Still there is a problem. The insertion and removal of the vacuum tube does cause a great deal of pain and discomfort to the patient. The pain and discomfort are such that some people even put off getting necessary medical assistance.

Other problems with the vena puncture device involve the friction between the vacuum tube and the vena puncture device at the removal of the vacuum tube therefrom. If the vena puncture device is held too loosely while the vacuum tube is removed, the device might be removed from the vein. Such premature removal of the device from the vein requires a second puncture and abrogates the advantages of the device. If the vena puncture device is held too tightly while the vacuum tube is removed, the device might pass right through the vein. Such an injury is painful and undesirable.

Friction between the vacuum tube and vena puncture device can also be a problem. The device must be small enough to guide the tube, while avoiding friction which causes pressure and pain. Avoidance of friction can create a size too large to provide guidance of the vacuum tube. Guidance for the vacuum tube can create a size for the vena puncture device too small to avoid friction.

An apparatus designed to solve these problems must be simple to operate and not increase the bulk of the vena puncture device in any substantial fashion. If a method and an apparatus can be developed which minimizes this pain by simplifying the insertion or withdrawal of the vacuum tube without unduly increasing the size or the difficulty of operation, great advantages in reduction of pain and increase in the comfort of the patient are obtained.

SUMMARY OF THE INVENTION

Accordingly, among the many objects of this invention is to provide an improved vena puncture device capable of assisting with the removal of the vacuum tube.

A further object of this invention is to provide an improved vena puncture device which simplifies withdrawal of a substantial number of blood samples from a patient.

A still further object of this invention is to provide an improved vena puncture device which reduces pain to a patient caused by removal of vacuum tube from a vena puncture device.

Yet a further object of this invention is to provide an improved vena puncture device which reduces discomfort to a patient caused by removal of vacuum tube from a vena puncture device.

Also an object of this invention is to provide an improved vena puncture device which minimizes the chance of a patient putting off needed tests.

Another object of this invention is to provide an improved vena puncture device which is simple to operate.

Yet another object of this invention is to provide an improved vena puncture device which has a minimal increase in bulk.

Still another object of this invention is to provide an improved vena puncture device which simplifies insertion of the vacuum tube into the vena puncture device.

A further object of this invention is to provide an improved vena puncture device which reduces the possibility of premature withdrawal of the vena puncture device.

A still further object of this invention is to provide an improved vena puncture device which reduces the possibility the vena puncture device passing through the vein.

Yet a further object of this invention is to provide an improved vena puncture device which reduces friction between a vacuum tube and a vena puncture device.

Also an object of this invention is to provide an improved method for drawing blood from a patient.

These and other objects (which other objects become clear by consideration of the specification, drawings and claims as a whole) of the invention are met by providing an improved vena puncture device having a spring-loaded device to assist with the removal of a vacuum tube.

BRIEF DESCRIPTION OF THE DRAWINGS

Throughout the Figures of the drawings when the same part is used in more than one Figure of the drawing, the same number is applied thereto.

DESCRIPTION OF THE PREFERRED EMBODIMENTS

A vena puncture device has a modified vena tube to provide for a spring loaded assembly within the vena tube. With the spring loaded assembly, the compressed spring of the vena puncture device provides for simplified removal of a vacuum tube. Latches release the compressed spring assembly forcing the vacuum tube out of the vena tube and minimizing the pulling on the needle thereby easing the pain to the patient.

Figure 1:
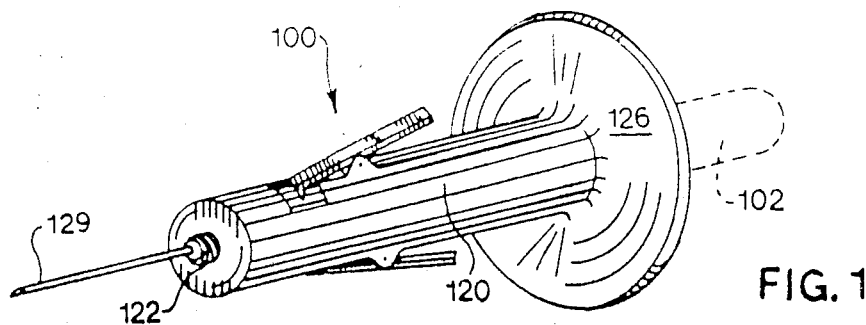
FIG. 1 is a perspective view of the vena puncture device 100 of this invention.
Figure 2:
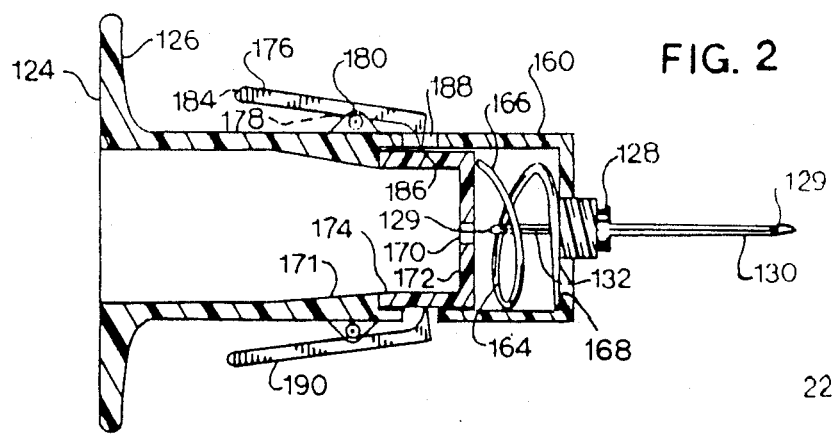
FIG. 2 is a side cross section of vena puncture device 100 of this invention showing the spring assembly 160.
Figure 3:
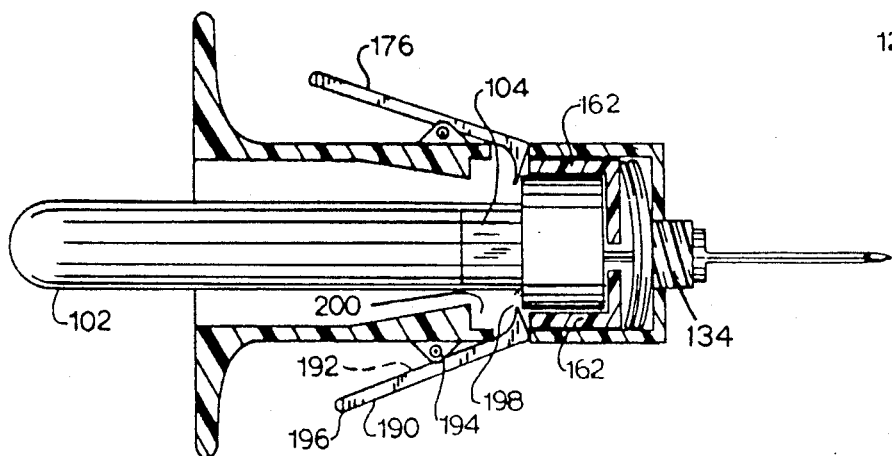
FIG. 3 is a depiction of FIG. 2 having vacuum tube 102 inserted with the spring assembly 160 compressed.

Referring now to FIG. 1, FIG. 2 and FIG. 3, spring-loaded vena puncture device 100 includes a flanged vena tube 120. The flanged vena tube 120 has needle end 122 and a vacuum end 124 oppositely disposed therefrom. Within the vena tube 120, is an inner vena tube flange 171. A two ended needle 128 is threadably or otherwise suitably mounted in a central portion of the substantially closed needle end 122—thereby closing the vena tube 120 at the needle end 122 except for the aperture 129 of needle 128.

The vein end 130 of needle 128 punctures the vein of a patient. Vein end 130 extends outside of vena tube 120. The tube end 132 of needle 128 is within the vena tube 120 and adjacent needle end 122. The needle mount 134 is centrally mounted in needle end 122 and has needle 128 secured thereto.

Spring assembly 160 is situated in vena tube 120 between the outer tube flange 126 and needle end 122. The spring assembly 160 includes a U-shaped spring compressor 162 in the form of a cylinder and a coil spring 164 to be compressed thereby.

Outer tube flange 126 is at vacuum end 124 of flanged vena tube 120. Outer tube flange 126 is circular in nature with a larger diameter than flanged vena tube 120. This outer tube flange 126 provides a proper angle for insertion of the spring-loaded vena puncture device 100 into a vein.

The U-shaped compressor 162 circles the interior of vena tube 120. Coil spring 164 is between U-shaped compressor 162 and needle end 122. Coil spring 164 has a compression end 166 adjacent to U-shaped compressor 162 and a tube end 168 adjacent needle end 122.

Centrally located in U-shaped compressor 162 is a compressor aperture 170 to receive vein end 130 of needle 128. The U-shaped compressor 162 includes substantially closed end in the form of base 172 of generally circular nature having compressor aperture 170 centrally located therein. Compressor flange 174 is substantially cylindrical in shape and protrudes from base 172 to form U-shaped compressor 162 and protrude upwardly toward outer tube flange 126 and interior tube flange 171.

Thus, when coil spring 164 is not compressed, compressor flange 174 contacts interior tube flange 171. When coil spring 164 is compressed, first latch 176 and second latch 190 combine to hold base 172 of U-shaped compressor 162 adjacent needle end 122 thereby compressing coil spring 164. When first latch 176 and second latch 190 release U-shaped compressor 162, coil spring 164 applies force to assist in removing vacuum tube 102. The user of vena puncture device 100 must still apply some pulling power, but coil spring 164 provides assistance—especially in overcoming the friction between tube end 132 of needle 128 and vacuum seal 104 of vacuum tube 102.

First latch 176 is mounted with a first bar spring 178 on a first latch pivot 180. First latch 176 includes a first latch grip 184 on one end thereof capable of being squeezed and a first latch point 186 oppositely disposed therefrom capable of passing through the first latch aperture 188 in vena tube 120 into contact with compressor flange 174 in order to hold U-shaped compressor 162 adjacent needle end 122 thereby compressing coil spring 164.

In the same fashion, diametrically opposed on vena tube 120 is second latch 190. Second latch 190 also has a second bar spring 192 to hold second latch 190 in position. The second latch pivot 194 supports second latch 190. Second latch grip 196 is activated by second latch bar spring 192 in order to hold second latch point 198 within second latch aperture 200 in vena tube 120 and thereby position U-shaped compressor 162 adjacent needle end 122. In this fashion, the coil spring 164 is compressed.

Coil spring 164 can be compressed by inserting vacuum tube 102 within U-shaped compressor 162 and pushing. With tube end 122 of needle 128 coming through compressor aperture 170, vacuum tube 102 has vacuum seal 104 punctured. The vacuum in vacuum tube 104 then withdraws blood through needle 128 into vacuum tube 102. When it is desired to remove vacuum tube 102 from vena tube 120, first latch grip 184 and second latch grip 196 of spring assembly 160 are pressed thereby removing second latch point 198 from second latch aperture 200 and first latch point 186 from first latch aperture 188 thereby releasing U-shaped compressor 162 which is forced adjacent inner tube flange 171 and consequently forces vacuum tube 102 and vacuum seal 104 off of needle 128 at tube end 132.

In this fashion, vacuum tube 102 can be removed from needle 128 with minimal pain and discomfort to the patient. Appropriately, a second vacuum tube 102 may be inserted in U-shaped compressor 162 and compressed coil spring 164 until vein end 130 of needle 128 punctures vacuum seal 104 thereby filling second vacuum tube 102 with blood. The release of the second of vacuum tube 102 is substantially similar to the release of the first of vacuum tube 102. Thus, the numbers of vacuum tube 102 that are desired to be filled can be filled with minimal pain or discomfort to patient. Spring assembly 160 minimizes movement of the needle 128 and has a direct effect on minimizing pain or discomfort during the blood drawing from a patient.

Figure 4:
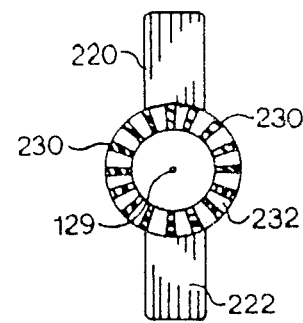
FIG. 4 is an end view of vena puncture device 100 of this invention from vacuum end 124.

Referring now to FIG. 4, an end view of the spring-loaded vena puncture device 100 shows a change from outer flange 126 and inner vena tube flange 171 as depicted in FIG. 1. A first ear flange 220 and a second ear flange 222 replace outer tube flange 126 as an assist for insertion of the spring-loaded vena puncture device 100 into a vein. Needle aperture 129 is also shown. The first ear flange 220 and a second ear flange 222 are flat, diametrically opposed protuberances serving a similar function as outer flange 126 except for the insertion assistance which falls back on the user.

Additionally, inner flange 171 is replaced by a series of ridges 230. Ridges 230 reduce the diameter of vena tube 120 to that of U-shaped compressor 162. Ridges 230 are diametrically placed uniformly around the interior vena tube 120 and do not completely encircle vena tube 126 as does inner flange 171. Any number of ridges 230 may be uniformly spaced therearound. The ridge spaces 232 between ridges 230 reduce friction on vacuum tube 102 during removal or and provide for easier insertion thereof onto tube end 132 of needle 128. Like interior flange 171, ridges 230 hold spring loaded assembly 160 within vena tube 120.

Any number of ridges 230 may be used. Preferably at least two ridges 230 are used. More preferably, three to 30 of ridges 230 may be used. Most preferably 10 to 20 of ridges 230 may be used. Also preferably each ridge space 232 has a size of fifty (50%) to one hundred fifty (150%) percent of each ridge 230 More preferably each ridge space 232 has a size of sixty (60%) to one hundred forty (140%) percent of each ridge 230. Most preferably each ridge space 232 has a size of seventy five (75%) to one hundred twenty five (125%) percent of each ridge 230.

Spring-loaded vena puncture device 100 can be used to draw liquid from any suitable source. The primary use is drawing blood from a human being. It can also be used for drawing blood from other animals or other liquid sources.

This application—taken as a whole with the specification, claims, abstract, and drawings—provides sufficient information for a person having ordinary skill in the art to practice the invention disclosed and claimed herein. Any measures necessary to practice this invention are well within the skill of a person having ordinary skill in this art after that person has made a careful study of this disclosure.

Because of this disclosure and solely because of this disclosure, modification of this method and apparatus can become clear to a person having ordinary skill in this particular art. Such modifications are clearly covered by this disclosure.

What is claimed and sought to be protected by letters Patent by the United States is:

1. A vena puncture device for receiving a vacuum tube with a rupturable seal, said vena puncture device including a vena tube having a spring loaded assembly operably mounted within said vena tube, wherein:
   a. said vena tube has a needle end at one end of said vena tube and an open vacuum end oppositely disposed from said needle end;
   b. a two-ended needle is removably and centrally mounted within said needle end;
   c. a restraining means is secured within said vena tube between said needle ned and said vacuum end;
   d. said spring loaded assembly is slidably mounted within said vena tube between said needle end and said restraining means;
   e. said two-ended needle is a hollow tube capable of passing blood therethrough;
   f. said two-ended needle has a vein end extending outside of said vena tube to puncture a vein of a patient;
   g. said two-ended needle has a tube end extending inside of said vena tube capable of puncturing said rupturable seal;
   h. said vein end is oppositely disposed from said tube end;
   i. a releasable locking means for releasably secures said spring loaded assembly in a compressed spring mode;
   j. said spring loaded assembly includes a cylindrical compressing means, having an open, tube-receiving end and a substantially closed end oppositely disposed from said open tube-receiving end;
   k. said tube-receiving end contacts said restraining means when said compressible spring is in an uncompressed mode;
   l. said open tube-receiving end is removed from said restraining means when said compressible spring is in a compressed mode;
   m. said substantially closed end is removed from said needle end when said compressible spring is in an uncompressed mode;
   n. said substantially closed end is adjacent said needle end when said compressible spring is in an compressed mode; and
   o. said restraining means is an interior tube flange.

2. The vena puncture device of claim 1, wherein:
   a. said spring loaded assembly includes said releasable locking means, a spring compressing means, and a compressible spring means;
   b. said spring compressing means of spring loaded assembly is slidably mounted within said vena tube between said needle end and said restraining means;
   c. said spring compressing means is cylindrical in having an open, tube-receiving end and a substantially closed end oppositely disposed from said open end;
   d. said substantially closed end has an aperture centrally located therein for receiving said tube end of said needle;
   e. said open tube-receiving end is adjacent said restraining means;
   f. said closed end is adjacent said needle end and contacts said compressible spring means; and
   g. said compressible spring means contacts said needle end.

3. The vena puncture device of claim 2 wherein said compressible spring means is a coil spring.

4. The vena puncture device of claim 2 wherein:
   a. said releasable locking means includes a first latch mounted on said vena tube;
   b. said releasable locking means further includes a second latch mounted on said vena tube;
   c. said first latch is diametrically opposed to said second latch;
   d. said first latch is pivotally mounted on said vena tube;
   e. said second latch is pivotally mounted on said vena tube;
   f. said first latch includes a first latch grip at a first end thereof capable of receiving pressure and a first latch point at second end thereof oppositely disposed from said first latch grip; and
   g. said second latch includes a second latch grip at a first end thereof capable of receiving pressure and a second latch point at second end thereof oppositely disposed from said second latch grip.

5. The vena puncture device of claim 2 wherein:
   a. said first latch point passes through a first latch aperture in said vena tube;
   b. said second latch point passes through a second latch aperture in said vena tube:
   c. said first latch point and said second latch point contact said compressor flange to hold said U-shaped compressor adjacent needle end when said compressible spring means is in a compressed mode; and
   d. said first latch grip and said second latch grip provide for said first latch point and said second latch point to release said compressor flange and place compressible spring means in an uncompressed mode.

6. The vena puncture device of claim 5 wherein:
   a. said first latch is springloaded to provide contact of first latch point with said first latch aperture;
   b. said second latch is springloaded to provide contact of second latch point with said second latch aperture;
   c. said first latch is springloaded by a first bar spring;

d. said second latch is springloaded by a second bar spring;
e. said compressible spring means is compressible by insertion of said vacuum tube.

7. The vena puncture device of claim 6 wherein:
a. said vacuum end of said vena tube includes a first ear flange and oppositely disposed second ear flange to assist an insertion of said vena puncture device;
b said holding means includes at least one interior ridge on an interior of said vena tube to hold said spring-loaded assembly within said vena tube.

8. The vena puncture device of claim 7 wherein said at least one interior ridge includes at least six ridges.

9. The vena puncture device of claim 7 wherein:
a. said substantially closed end has an aperture centrally located therein for receiving said tube end of said needle;
b. said open tube-receiving end is adjacent said restraining means;
c. said closed end is adjacent said needle end and contacts said compressible spring means;
p. said compressible spring means contacts said needle end;
q. said compressible spring means is a coil spring;
r. said vacuum end of said vena tube includes a circular flange to assist an insertion of said vena puncture device;
s. said holding means is an interior flange circling an interior of said vena tube to hold said spring-loaded assembly within said vena tube.

10. The vena puncture device of claim 6 wherein:
a. said compressible spring means contacts said needle end; and
b. said compressible spring means is a coil spring;
c. said vacuum end of said vena tube includes a circular flange to assist an insertion of said vena puncture device; and
d. said holding means is an interior flange circling an interior of said vena tube to hold said spring-loaded assembly within said vena tube.

11. The vena puncture device of claim 6 wherein:
a. said vacuum end of said vena tube includes a circular flange to assist an insertion of said vena puncture device;
b. said holding means is an interior flange circling an interior of said vena tube to hold said spring-loaded assembly within said vena tube.

12. The vena puncture device of claim 6 wherein:
a. said vacuum end of said vena tube includes a first ear flange and oppositely disposed second ear flange to assist an insertion of said vena puncture device;
b. said holding means includes at least one interior ridge on an interior of said vena tube to hold said spring-loaded assembly within said vena tube.

13. The vena puncture device of claim 12 wherein said at least one ridge includes at least six diametrically and symmetrically spaced ridges.

14. The vena puncture device of claim 1 wherein:
a. said open tube-receiving end contacts said restraining means when said compressible spring is in an uncompressed mode;
b. said open tube-receiving end is removed from said restraining means when said compressible spring is in an compressed mode;

c. said substantially closed end is removed from said needle end when said compressible spring is in an uncompressed mode;
d. said substantially closed end is adjacent said needle end when said compressible spring is in an compressed mode;
e. said restraining means is an interior tube flange;
f. said releasable locking means includes a first latch mounted on said vena tube;
g. said releasable locking means further includes a second latch mounted on said vena tube;
h. said first latch is diametrically opposed to said second latch;
i. said first latch is pivotally mounted on said vena tube;
j. said second latch is pivotally mounted on said vena tube;
k. said first latch includes a first latch grip at a first end thereof capable of receiving pressure and a first latch point at second end thereof oppositely disposed from said first latch grip;
l. said second latch includes a second latch grip at a first end thereof capable of receiving pressure and a second latch point at second end thereof oppositely disposed from said second latch grip;
m. said first latch point passes through a first latch aperture in said vena tube;
n. said second latch point passes through a second latch aperture in said vena tube;
o. said first latch point and said second latch point contact said compressor flange to hold said U-shaped compressor adjacent needle end when said compressible spring means is in a compressed mode; and
p. said first latch grip and said second latch grip provide for said first latch point and said second latch point to release said compressor flange and place compressible spring means in an uncompressed mode 15. The vena puncture device of claim 14 wherein:
a. said first latch is springloaded to provide contact of first latch point with said first latch aperture;
b. said second latch is springloaded to provide contact of second latch point with said second latch aperture;
c. said first latch is springloaded by a first bar spring;
d. said second latch is springloaded by a second bar spring; and
e. said compressible spring means is compressible by insertion of said vacuum tube.

16. The vena puncture device of claim 14 wherein wherein an inner vena tube flange provides a holding means for holding said spring loaded assembly adjacent said needle end.

17. The vena puncture device of claim 16 wherein:
a. said vacuum end of said vena tube includes a first ear flange and oppositely disposed second ear flange to assist an insertion of said vena puncture device; and
b. said holding means includes at least one interior ridge on an interior of said vena tube to hold said spring-loaded assembly within said vena tube.

18. A vena puncture device for receiving a vacuum tube with a rupturable seal, said vena puncture device including a vena tube having a spring loaded assembly operably mounted within said vena tube, wherein:

a. said vena tube has a needle end at one end of said vena tube and an open vacuum end oppositely disposed from said needle end;
b. a two-ended needle is removably and centrally mounted within said needle end;
c. a restraining means is secured within said vena tube between said needle end and said vacuum end;
d. said spring loaded assembly is slidably mounted within said vena tube between said needle end and said restraining means;
e. said two-ended needle is a hollow tube capable of passing blood therethrough;
f. said two-ended needle has a vein end extending outside of said vena tube to puncture a vein of a patient;
g. said two-ended needle has a tube end extending inside of said vena tube capable of puncturing said rupturable seal;
h. said vein end is oppositely disposed from said tube end;
i. a releasable locking means for releasably securing said spring loaded assembly in a compressed spring mode;
j. said spring loaded assembly includes said releasable locking means, a spring compressing means, and a compressible spring means;
k. said spring compressing means of spring loaded assembly is slidably mounted within said vena tube between said needle end and said restraining means;
l. said spring compressing means is cylindrical in having an open, tube-receiving end and a substantially closed end oppositely disposed from said open end;
m. said substantially closed end has an aperture centrally located therein for receiving said tube end of said needle;
n. said open tube-receiving end is adjacent said restraining means;
o. said closed end is adjacent said needle end and contacts said compressible spring means;
p. said compressible spring means contacts said needle end;
q. said compressible spring means is a coil spring:
r. said vacuum end of said vena tube includes a circular flange to assist an insertion of said vena puncture device; and
s. said holding means is an interior flange circling an interior of said vena tube to hold said spring-loaded assembly within said vena tube.

* * * * *